United States Patent [19]

Lang et al.

[11] Patent Number: 4,739,099
[45] Date of Patent: Apr. 19, 1988

[54] 1-SUBSTITUTED 4-METHOXY-2,3,6-TRIMETHYLBENZENE DERIVATIVES, AND MEDICINAL AND COSMETIC COMPOSITIONS CONTAINING THESE DERIVATIVES

[75] Inventors: Gérard Lang, Saint Gratien; Serge Forestier, Claye-Souilly; Alain Lagrange, Chatou; Braham Shroot, Antibes, all of France

[73] Assignee: L'Oreal, Paris, France

[21] Appl. No.: 781,634

[22] Filed: Sep. 30, 1985

[30] Foreign Application Priority Data

Oct. 1, 1984 [LU] Luxembourg .................. 85.562

[51] Int. Cl.$^4$ .......................................... C07C 69/76
[52] U.S. Cl. ..................................... 560/56; 562/466; 564/180; 568/328; 568/441; 568/607; 568/612; 568/613; 558/401; 558/423; 548/240; 549/427; 424/308; 424/275; 424/285; 424/317; 424/324; 424/331; 424/339
[58] Field of Search ............... 560/56; 562/466; 564/180; 568/328, 441, 607, 612, 613; 558/401, 423; 548/240; 549/427; 424/308, 275, 285, 317, 324, 331, 334

[56] References Cited

U.S. PATENT DOCUMENTS 4,456,618  6/1984  Dawson et al. .................. 560/56

FOREIGN PATENT DOCUMENTS 2150563  7/1985  United Kingdom .................. 560/56

Primary Examiner—Paul J. Killos
Attorney, Agent, or Firm—Cushman, Darby & Cushman

[57] ABSTRACT

The invention provides a compound of formula (II):

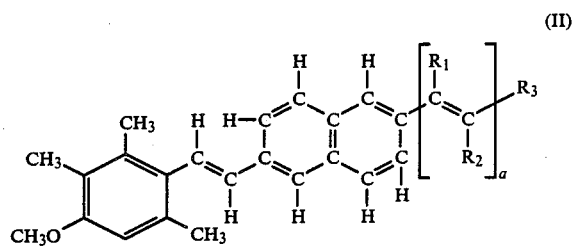

and the corresponding isomers and salts; in this formula, a equals 0 or 1; $R_1$ and $R_2$ represent, independently, H or a $C_1$-$C_4$ alkyl group; $R_3$ denotes —C≡N; oxazolinyl; —CH$_2$OR$_4$ (R$_4$=H, $C_1$-$C_4$ alkyl, $C_2$-$C_6$ mono- or polyhydroxyalkyl, cyclopentyl or cyclohexyl, or —OR$_4$=tetrahydropyranyl); —COR$_5$ (R$_5$=H, $C_1$-$C_4$ alkyl, —NR'R" where R' and R" have various meanings); —OR$_6$ (R$_6$=H, $C_1$-$C_{18}$ alkyl, $C_2$-$C_3$ monohydroxyalkyl or $C_3$-$C_6$ polyhydroxyalkyl with 2-5 OH groups), which has useful medicinal and cosmetic applications.

29 Claims, No Drawings

1-SUBSTITUTED 4-METHOOXY-2,3,6-TRIMETHYLBENZENEDERVATIVES, AND MEDICINAL AND COSMETIC COMPOSITIONS CONTAINING THESE DERIVATIVES

The invention relates to new 1-substituted 4-methoxy-2,3,6-trimethyl benzene derivatives, as well as to the process of preparation by which these new compounds may be obtained. The invention also relates to the use of these new compounds, either in cosmetics, or as pharmaceutical preparations in the treatment of dermatological conditions linked to a disorder of keratinisation (differentiation/proliferation), in the treatment of dermatological or other conditions involving an inflammatory and/or immuno-allergic component, in the treatment of degenerative diseases of the conjunctival tissue and tumours, and in the treatment of rheumatoid psoriasis, or as pharmaceutical preparations for the ophthalmic field, especially in the treatment of corneopathies. Moreover, these products can be used in the treatment of cutaneous atropy, such as eczema.

The therapeutic action of vitamin A in its acid, aldehyde or alcohol form is well known in dermatology [see, in this context, the publication "EXPERIENTIA", volume 34, pages 1105-1119 (1978)]; this action in the treatment of cutaneous proliferations, acne, psoriasis and similar conditions will hereafter be referred to by the generic term "retinoid-type action". It has been found that products having a structure analogous to vitamin A also exhibit a retinoid-type action, but that the side effect of toxic hypervitaminosis can, in the case of some compounds, be boosted by a smaller factor than the boosting factor of the desired retinoid-type effect (see, in this context, "EUR. J. MED. CHEM.—CHIMICA THERAPEUTICA", January/February 1980, 15, No. 1, pages 9-15); P. Loeliger et al. have, in this latter publication, described a derivative of the formula (I):

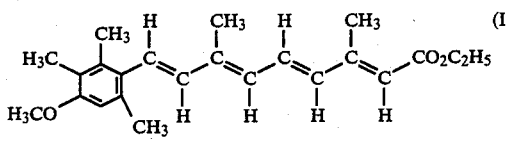

It has been found, according to the invention, that the substituent chain of the compound of formula (I) could be replaced by a different substituent chain comprising a naphthalene system, without thereby losing the benefit of the retinoid-type action of these compounds.

The invention accordingly provides a chemical compound corresponding to the general formula (II):

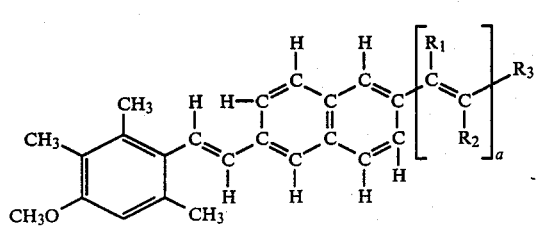

and the corresponding isomers and salts, in which formula:

a is equal to 0 or 1;
$R_1$ and $R_2$ represent, independently, a hydrogen atom or a $C_1$-$C_4$ alkyl radical;
$R_3$ represents:
a C≡N radical;
an oxazolinyl radical;
a radical of formula (III):

$$-CH_2OR_4 \qquad (III)$$

in which formula $R_4$ represents a hydrogen atom, a $C_1$-$C_4$ alkyl radical, a $C_2$-$C_6$ mono- or polyhydroxyalkyl radical, or a cyclopentyl or cyclohexyl radical, $OR_4$ being able, in addition, to represent a tetrahydropyranyl radical;
a radical corresponding to the formula (IV):

in which formula $R_5$ represents:
(a) a hydrogen atom, a $C_1$-$C_4$ alkyl radical, an —NR'R" radical, R' and R", which may be identical or different, representing a hydrogen atom, a $C_1$-$C_4$ alkyl radical, a $C_3$-$C_4$ alkenyl radical, a cyclopentyl or cyclohexyl radical, or an optionally substituted aralkyl or aryl radical, R' and R" being able to form a heterocyclic system with the nitrogen atom to which they are attached, the —NR'R" radical also being able to be an amino acid residue or glucosamine residue;
(b) an —$OR_6$ radical, where $R_6$ represents a hydrogen atom, a $C_1$-$C_{18}$ alkyl radical, a $C_2$-$C_3$ monohydroxyalkyl radical, or a $C_3$-$C_6$ polyhydroxyalkyl radical containing 2 to 5 hydroxyl groups.

Amongst the $C_1$-$C_{18}$ alkyl radicals which are particularly useful in respect of the meanings of the radical $R_6$, preferential mention can be made of methyl, ethyl, propyl, 2-ethylhexyl, octyl, dodecyl, hexadecyl and octadecyl radicals.

Among the $C_1$-$C_4$ alkyl radicals which are particularly useful in respect of the meanings of the radicals $R_1$, $R_2$, $R_4$, R' and R", there can be mentioned methyl, ethyl isopropyl, butyl and tert-butyl radicals, and preferably, for $R_1$ and $R_2$, the methyl radical.

When the radical $R_4$ or $R_6$ represents a monohydroxyalkyl radical, the latter is preferably a 2-hydroxyethyl or 2-hydroxypropyl radical.

When the radical $R_4$ or $R_6$ represents a polyhydroxyalkyl radical, the latter is preferably 2,3-dihydroxypropyl, 2,3,4-trihydroxybutyl or 2,3,4,5-tetrahydroxypentyl or the pentaerythritol residue.

Among the substituted or unsubstituted aryl radicals which are particularly useful in respect of the meanings of the radicals R' and R", the phenyl radical, optionally substituted with a halogen atom or a hydroxyl or $C_1$-$C_4$ alkoxy group, is preferred.

Among the aralkyl radicals which are particularly useful in respect of the meanings of the radicals R' and R", the benzyl radical or phenethyl radical optionally substituted with a hydroxyl or alkoxy group is preferred.

When the radicals R' and R" form a heterocyclic system with the nitrogen atom to which they are attached, the system formed is preferably a piperidino, morpholino, piperazino, pyrrolidino or 4-(2-hydroxyethyl)piperazino radical.

Especially preferred compounds of formula (II) are those for which a equals 0 or 1, $R_1$ and $R_2$ represent, independently of each other, a hydrogen atom or a methyl radical, and $R_3$ denotes a carboxyl or alkoxycarbonyl radical, a formyl or hydroxymethyl radical, or an aminocarbonyl radical.

The compounds of formula (II) and the isomers thereof can take the form of their salts; these can be, e.g., zinc, alkali metal or alkaline earth metal salts or salts with an organic amine when they contain at least one free acidic group, or they can be salts with an inorganic or organic acid, in particular hydrochloride, hydrobromide or citrate, when they contain at least one amine group.

The invention provides all the isomers of the compounds of general formula (II) and to the salts thereof.

The invention also provides a process for preparing the compounds of formula (II). According to the invention, the synthesis of the compounds of formula (II) consists in reacting a compound of formula (V):

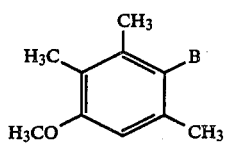

(V)

with a compound of formula (VI):

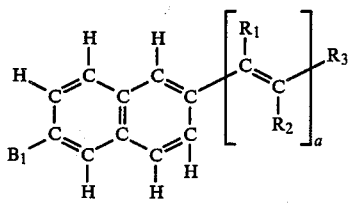

(VI)

in which formulae $R_1$, $R_2$, $R_3$ and a have the meanings indicated above, with the proviso that $R_3$ cannot represent the group of formula (IV) when $R_5$ is a hydrogen atom or a $C_1$–$C_4$ alkyl radical. In the formulae (V) and (VI), one of the groups B and $B_1$ represents a carbonyl group while the other is:

(a) either a methylenetriarylphosphonium group of formula (VII):

(VII)

where X is an aryl group and Y a monovalent anion of an organic or inorganic acid; or (b) a methylenedialkoxyphosphinyl group of formula (VIII):

(VIII)

where Z represents a $C_1$–$C_4$ alkoxy group.

When one of B and $B_1$ represents a carbonyl and the other represents a methylenetriarylphosphonium group, the reaction is suitably performed in the presence of an alkali metal alcoholate, such as sodium methylate, or in the presence of an alkylene oxide optionally substituted with an alkyl group, in particular in a solvent such as methylene chloride or dimethylformamide. The reaction temperature is from room temperature to the boiling point of the reaction mixture.

When one of B and $B_1$ represents a carbonyl and the other represents a methylenedialkoxyphosphinyl group, the reaction is suitably performed in the presence of a base, and preferably in the presence of an inert organic solvent; the reaction can be accomplished, for example, by means of sodium hydride in benzene, toluene, dimethylformamide, tetrahydrofuran, dioxane or 1,2-dimethoxyethane, or also by means of an alcoholate, for example by means of sodium methylate, in methanol; the reaction is preferably performed in a temperature range from 0° C. to the boiling point of the reaction mixture. The condensation can also be carried out using an inorganic base, such as potassium hydroxide or sodium hydroxide, in an organic solvent such as tetrahydrofuran. A crown ether capable of complexing the metal cation present in the base can also be added to the reaction mixture, and this enables the power of the base to be increased.

Compounds of formula (V) and (VI) are known compounds, or can be prepared by known methods.

The compound of formula (II) obtained by the preparation process according to the invention can undergo functional modifications of the substituent $R_3$. Among the functional modifications of this substituent $R_3$, there will be mentioned, for example, the saponification of a carboxylic acid ester or the reduction of the carboxylic acid ester group to hydroxymethyl group. The hydroxymethyl group can also be oxidised to a formyl group, or alternatively esterified or etherified. Furthermore, a carboxyl group may be converted to a salt, an ester, an amide, an alcohol or an acetyl group, or to the corresponding acid chloride. A carboxylic acid ester group can be converted to an acetyl group. The acetyl group can be converted to a secondary alcohol group by reduction, and the secondary alcohol group can itself by alkylated or acylated using known procedures. All these functional modifications can be carried out by procedures known per se.

Compounds of formula (II) are usually obtained in the form of cis/trans mixtures which can, if desired, be separated in a manner known per se into the cis and trans compounds, or isomerised to all-trans compounds.

According to the invention, it has been found that the compounds of formula (II) have a retinoid-type action and are particularly suitable for the treatment of dermatological conditions linked to a disorder of keratinisation (differentiation/proliferation) as well as dermatological or other conditions which involve an inflammatory and/or immuno-allergic component, in particular for the treatment of acnes, degenerative diseases of the conjunctival tissue, extensive and/or severe forms of psoriasis, other disorders of keratinisation, and in particular ichthyoses and ichthyosiform states, Darier's disease, keratoderma palmaris et plantaris, leukoplakia and leukoplakiform states, lichen planus and all severe or extensive dermatological proliferations, whether benign or malignant. These compounds are also active for rheumatoid psoriasis. In addition, these compounds can be used in the treatment of cutaneous atropy such as eczema. Again, these compounds can be used in the ophthalmic field in the treatment of corneopathies.

The present invention thus also provides a medicinal composition, intended in particular for the treatment of the abovementioned conditions, which comprises at least one compound of formula (II) and/or one of its salts, in a pharmaceutically acceptable base.

If the compounds according to the invention are used topically, it is found that they exhibit good activity over a very broad concentration; in particular concentrations of the active product from 0.0005% to 2% by weight, relative to the total weight of the composition, can be used. It is of course possible to use higher concentrations if this should become necessary for a particular therapeutic application; however, the preferred concentrations of an active product is from 0.002% to 1% by weight.

The topical compositions are advantageously in the form of unguents, ointments, dyeing compositions, solutions, gels, creams, suspensions, emulsions, lotions, powders, sprays, adhesive patches and impregnated pads. The compounds according to the invention can be mixed with inert, nontoxic, generally liquid or pasty bases suitable for topical treatment.

The compounds according to the invention can also be used enterally. Orally, the compounds according to the invention are suitably administered at the rate of 2 $\mu$g to 2 mg per day per kg of body weight; an excessive posology can reveal itself as a hypervitaminosis A, recognisable from its symptoms and from a possible liver toxicity necessitating biological control of the hepatic function. The required dose can be administered in one or more portions. For oral administration, suitable forms are, for example, tablets, gelatin capsules, dragées, syrups, suspensions, emulsions, solutions, powders and granules; a preferred method of administration consists in using gelatin capsules containing from 0.1 mg to 1 mg of active product.

The compounds according to the invention can also be administered parenterally in the form of solutions or suspensions for intravenous or intramuscular perfusions or injections. In this case, the compounds according to the invention are suitably administered at the rate of 2 $\mu$g to 2 mg per day per kg of body weight; a preferred method of administration consists in using solutions or suspensions containing approximately from 0.01 mg to 1 mg of active product per ml. When the compounds according to the invention are used for administration to the eye, they are advantageously in the form of solutions or of powders to be diluted to form eye drops.

The pharmaceutically acceptable base can comprise water, gelatin, lactose, starch, talc, liquid petrolatum, gum arabic, a polyalkylene glycol or magnesium stearate. The tablets, powders, dragées, granules or gelatin capsules can contain, for example, binders, fillers or pulverulent bases. The solutions, creams, suspensions, emulsions or syrups can contain, for example, diluents, solvents or thickeners.

Compounds of formula (II) according to the invention, their isomers and their salts, also find application in the cosmetics field, in particular in body hygiene and hair hygiene, and especially in the treatment of acne, seborrhoea and loss of hair, for encouraging fresh growth of hair, for combating the greasy appearance of the skin or hair, and in the treatment of physiologically dry skin. Finally, they have preventive and curative powder against the adverse effects of sunlight.

The present invention thus also provides a cosmetic composition, characterised in that it comprises, in a cosmetically acceptable base, at least one compound of formula (II) and/or one of its salts; this composition can be in the form of, for example, a lotion, gel, cream, soap or shampoo.

In the case of a cosmetic composition, the compounds according to the invention can also be used over a very wide concentration range: concentrations of active product ranging from 0.0005 to 2% by weight, relative to the total weight of the composition, and preferably concentrations of 0.01 to 1% by weight, can advantageously be used.

In the treatment of the abovementioned disorders, the compounds according to the invention, used in the compositions defined above, act by increasing the follicular epithelial production of the non-adherent cells, thereby dislodging, and causing the loss of, the contents of the acne comedo. These compounds reduce the size of the sebaceous glands and partially inhibit the secretion of sebum.

The compounds according to the invention can be used with inert or pharmacodynamically or cosmetically active additives, depending on whether the composition is medicinal or cosmetic. These additives comprise, in particular, moisturising agents such as thiamorpholinone and its derivatives or urea; antiseborrhoeic agents such as S-carboxymethylcysteine, S-benzylcysteamine and their derivatives, tioxolone; anti-acne agents such as benzoyl peroxide; antibiotics such as erythromycin and its esters, neomycin, tetracyclines or 4,5-polymethylene-3-isothiazolones: agents which encourage fresh growth of hair, such as minoxidil (2,4-diamino-6-piperidinopyrimidine 3-oxide) and its derivatives, diazoxide(3-chloromethyl-1,2,4-benzothiadiazine 1,1-dioxide), phenytoin(5,5-diphenylimidazoline-2,4-dione) or oxapropanium iodide; antiinflammatory agents of a steroid or non-steroid type; carotenoids and especially $\beta$-carotene; and anti-psoriatic agents such as anthralin and its derivatives, eicosa-5,8,11,14-tetraynoic acid and eicosa-5,8,11-triynoic acid, their amides and their esters.

The compounds according to the invention can also contain flavourings, preservatives, stabilisers, moisture regulators, pH regulators, osmotic pressure modifiers, emulsifiers, UV-A and UV-B filters, and antioxidants such as $\alpha$-tocopherol, butylated hydroxyanisole or butylated hydroxytoluene.

The following Examples further illustrate the present invention.

EXAMPLE 1

Preparation of the compound of formula:

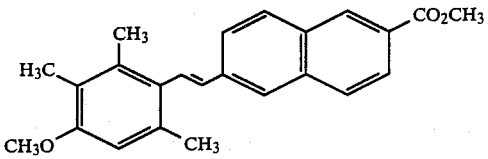

To a suspension of 10.1 g of (4-methoxy-2,3,6-trimethylbenzyl)triphenylphosphonium bromide in 50 cm³ of tetrahydrofuran, 10 cm³ of 2.5M butyllithium solution are added at $-30°$ C. under nitrogen. The temperature is allowed to rise to $0°$ C. during 30 min. The mixture is cooled to $-78°$ C. and 3.13 g of 6-methoxycarbonylnaphthaldehyde, dissolved in the minimum of dichloromethane, are then added. The mixture is stirred for one hour at $-78°$ C. and the temperature is then allowed to rise to $0°$ C. The mixture is extracted with ether after dilution with water. The organic phase is dried and the solvent distilled off. After chromatography on silica gel (eluant, toluene), the expected product is obtained in a yield of 60%. This product has the following properties:
Melting point: 169° C.

UV spectrum: $\begin{cases} \lambda\,\text{max} = 333\,\text{nm} \\ \epsilon = 24{,}000 \end{cases}$ (chloroform)

Elementary analysis:

|  | C | H | O |
|---|---|---|---|
| Calculated | 79.97 | 6.71 | 13.32 |
| Found | 79.80 | 6.80 | 13.06 |

EXAMPLE 2

Preparation of the compound of formula:

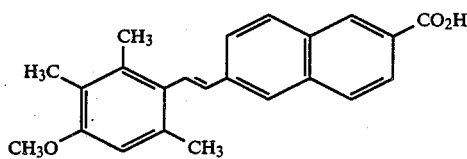

1.3 g of the compound obtained in Example 1 in 100 cm³ and 20 cm³ of 3N sodium hydroxide is heated for 2 hours under reflux. 30 cm³ of water are added; the methanol is then distilled off. After being cooled, the mixture is acidified with 3N hydrochloric acid. The precipitate obtained is filtered, washed with water and recrystallized in acetic acid (yield 62%). This product has the following properties:
Melting point: 252° C.

UV spectrum: $\begin{cases} \lambda\,\text{max} = 335\,\text{nm} \\ \epsilon = 25{,}600 \end{cases}$ (dimethyl sulphoxide)

Elementary analysis:

|  | C | H | O |
|---|---|---|---|
| Calculated | 79.74 | 6.40 | 13.86 |
| Found | 79.90 | 6.44 | 13.96 |

EXAMPLE 3

Preparation of the compound of formula:

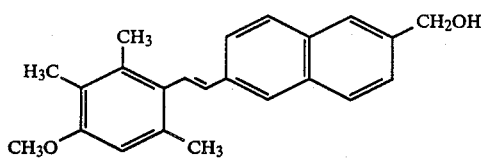

A solution of 3.3 g of the compound obtained in Example 2 in 30 cm³ of tetrahydrofuran is added slowly to a suspension of 0.35 g of lithium aluminum hydride in 20 cm³ of tetrahydrofuran. The mixture is stirred under nitrogen at 0° C. for one hour. At the end of the reaction, 5 cm³ of ethyl acetate are added and the mixture is then diluted slowly with water. The suspension is filtered on celite. The solvent is evaporated to dryness. 3 g of the expected product are obtained in the form of a colourless liquid which crystallises rapidly.

This product has the following properties:
Melting point: 138° C.

U.V. spectrum: $\begin{cases} \lambda\,\text{max} = 310\,\text{nm} \\ \epsilon = 20{,}000 \end{cases}$ (chloroform)

Elementary analysis:

|  | C | H | O |
|---|---|---|---|
| Calculated | 83.10 | 7.28 | 9.63 |
| Found | 83.20 | 7.30 | 9.85 |

EXAMPLE 4

Preparation of the compound of formula:

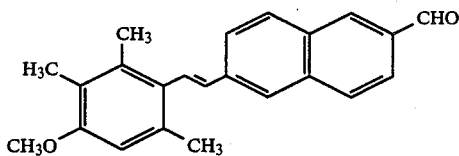

2.8 g of the compound obtained in Example 3 and 2.2 g of pyridinium chlorochromate in 50 cm³ of dichloromethane are stirred for 3 hours at room temperature. The reaction mixture is filtered on celite. The solvent is evaporated off and the product is purified by recrystallisation in ethanol. 1.7 g of the expected product is obtained.

This product has the following properties:
Melting point: 143° C.

U.V. spectrum: $\begin{cases} \lambda\,\text{max} = 350\,\text{nm} \\ \epsilon = 22{,}400 \end{cases}$ (chloroform)

Elementary analysis:

|  | C | H | O |
|---|---|---|---|
| Calculated | 83.60 | 6.71 | 9.68 |
| Found | 83.80 | 6.70 | 9.85 |

EXAMPLE 5

Preparation of the compound of formula:

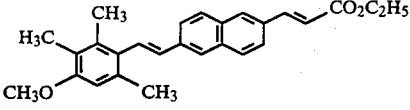

1.2 g of triethylphosphonoacetate is dissolved in 30 cm³ of tetrahydrofuran. 0.6 g of powdered potassium hydroxide is added and the mixture is stirred at room temperature for 15 min. A solution of 1.5 g of the compound obtained in Example 4 in 20 cm³ of tetrahydrofuran is added slowly. The mixture is stirred for two hours at room temperature. 50 cm³ of toluene are added and the reaction mixture is then filtered on celite. The filtrate is washed with water and the solvent is then evaporated. After recrystallisation in ethanol, 1.1 g of the expected product is obtained.

This product has the following properties:
Melting point: 148° C.

U.V. spectrum: $\begin{cases} \lambda\,max = 348\,nm \\ \epsilon = 32{,}000 \end{cases}$ (chloroform)

Elementary analysis:

|  | C | H | O |
|---|---|---|---|
| Calculated | 80.97 | 7.05 | 11.98 |
| Found | 81.14 | 7.09 | 11.68 |

EXAMPLE 6

Preparation of the compound of formula:

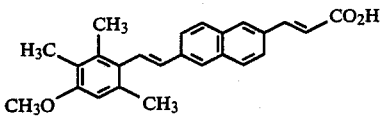

This compound is obtained by the procedure described in Example 2, in which the compound of Example 1 is replaced by the compound of Example 5. After recrystallisation in acetone, the expected product is obtained in an 82% yield. This product has the following properties:
Melting point: 210° C.

UV spectrum: $\begin{cases} \lambda\,max = 348\,nm \\ \epsilon = 30{,}000 \end{cases}$ (chloroform)

Elementary analysis:

|  | C | H | O |
|---|---|---|---|
| Calculated | 80.62 | 6.49 | 12.89 |
| Found | 80.55 | 6.54 | 12.77 |

EXAMPLE 7

The following formulation, designed to be packaged in a gelatin capsule, is prepared:

| Compound of Example 1 | 0.05 g |
|---|---|
| Maize starch | 0.06 g |
| Lactose qs | 0.3 g |

The gelatin capsules used consist of gelatin, titanium dioxide and a preservative.

1 to 3 gelatin capsules per day are administered to an adult person for the treatment of psoriasis, and a significant improvement is found after about 30 days.

EXAMPLE 8

A gel is prepared by producing the following formulation:

| Compound of Example 2 | 0.01 g |
|---|---|
| Erythromycin base | 4 g |
| Butylated hydroxytoluene | 0.05 g |
| Hydroxypropylcellulose sold by HERCULES under the name of "KLUCEL HF" | 2 g |
| Ethanol (95° strength) qs | 100 g |

This gel is applied on a skin suffering from dermatosis or a skin suffering from acne 1 to 3 times per day, and a significant improvement is found after a period of between 6 and 12 weeks, depending on the severity of the case treated.

EXAMPLE 9

An antiseborrhoeic lotion is prepared by producing the following formulation:

| Compound of Example 5 | 0.01 g |
|---|---|
| Propylene glycol | 5 g |
| Butylated hydroxytoluene | 0.1 g |
| Ethanol (95° strength) qs | 100 g |

This lotion is applied twice daily, and a significant improvement is found after a period of between 2 and 6 weeks.

EXAMPLE 10

A cosmetic composition for protection against sunlight is prepared by producing the following formulation:

| Compound of Example 2 | 0.5 g |
|---|---|
| Benzylidenecamphor | 4 g |
| Triglycerides of ($C_8$ to $C_{12}$) fatty acids | 31 g |
| Glycerol monostearate | 6 g |
| Stearic acid | 2 g |
| Cetyl alcohol | 1.2 g |
| Lanolin | 4 g |
| Preservatives | 0.3 g |
| Propanediol | 2 g |
| Triethanolamine | 0.5 g |
| Perfume | 0.4 g |
| Demineralised water qs | 100 g |

We claim:

1. A compound of the formula

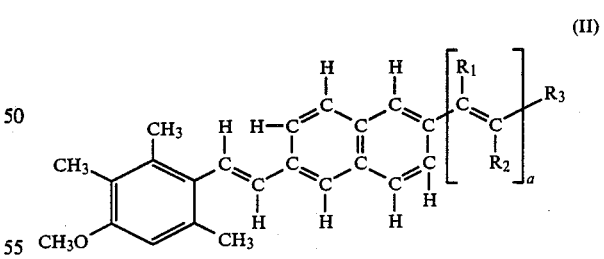

(II)

or an isomer or salt thereof, wherein
a is equal to 0 or 1;
$R_1$ and $R_2$ each independently represent hydrogen or alkyl having 1–4 carbon atoms,
$R_3$ represents
(i) —C≡N,
(ii) an oxazolinyl radical
(iii) —CH$_2$OR$_4$ wherein R$_4$ represents hydrogen, alkyl having 1–4 carbon atoms, mono or poly hydroxyalkyl having 2–6 carbon atoms, cyclopentyl, cyclohexyl, or OR$_4$ represents a tetrahydropyranyl radical, (iv) 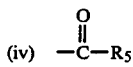

wherein $R_5$ represents (a) hydrogen, alkyl having 1–4 carbon atoms, —NR'R" wherein R' and R" each independently represent hydrogen, alkyl having 1–4 carbon atoms, alkenyl having 3–4 carbon atoms, cyclopentyl, cyclohexyl, aralkyl, aralkyl substituted by hydroxy or alkoxy, aryl, aryl substituted by halogen, hydroxy or alkoxy having 1–4 carbon atoms, or R' and R" together with the nitrogen atom to which they are attached form a heterocycle or NR'R" represent amino acid or glycosamine residue, or (b) —$OR_6$ wherein $R_6$ represents hydrogen, alkyl having 1–18 carbon atoms, monohydroxyalkyl having 2–3 carbon atoms, or poly hydroxyalkyl having 3–6 carbon atoms and 2–5 hydroxy groups.

2. A compound according to claim 1 in which $R_1$ and $R_2$ represent, independently, a hydrogen atom or a methyl radical, and $R_3$ denotes a carboxyl or alkoxycarbonyl radical, a formyl or hydroxymethyl radical or an aminocarbonyl radical.

3. A compound according to claim 1, which is in the form of a zinc, alkali metal or alkaline earth metal salt or a salt with an organic amine when the compound of formula (II) contains at least one free acidic group, or a salt with an inorganic or organic acid, when the compond of formula (II) contains at least one amine group.

4. A compound according to claim 3 in which the compound is in the form of a hydrochloride, hydrobromide or citrate.

5. Process for preparing a compound as defined in claim 1 which comprises reacting a compound of formula (V):

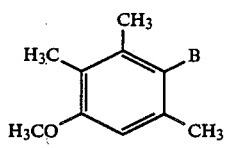 (V)

with a compound of formula (VI):

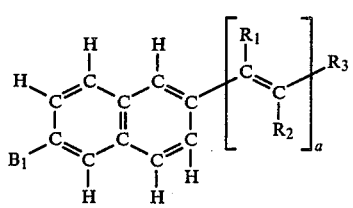 (VI)

in which formulae $R_1$, $R_2$, $R_3$ and a are as defined in claim 1, with the proviso that $R_3$ cannot represent the group of formula (IV):

 (IV)

when $R_5$ is a hydrogen atom or a $C_1$–$C_4$ alkyl radical; one of B and $B_1$ in formulae (V) and (VI) representing a carbonyl group while the other of B and $B_1$ is either:

(a) a methylenetriarylphosphonium group of formula (VII):

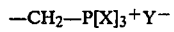 (VII)

where X is an aryl group and Y a monovalent anion of an organic or inorganic acid; or (b) a methylenedialkoxyphosphinyl group of formula (VIII):

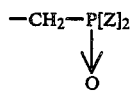 (VIII)

where Z represents a $C_1$–$C_4$ alkoxy group.

6. Process according to claim 5, in which one of B and $B_1$ represents a carbonyl group and the other represents a methylenetriarylphosphonium group, and the reaction is performed in the presence of an alkali metal alcoholate or an alkylene oxide optionally substituted with an alky group, in a solvent, the reaction temperature being from room temperature to the boiling point of the reaction mixture.

7. Process according to claim 6 in which the alcoholate is sodium methylate and the solvent is methylene chloride or dimethylformamide.

8. Process according to claim 5, in which one of B and $B_1$ represents a carbonyl group and the other represents a methylenedialkoxyphosphinyl group, and the reaction is performed in the presence of a base, the reaction temperature being from 0° C. to the boiling point of the reaction mixture.

9. Process according to claim 5 in which $R_3$ of the compound obtained by reaction of the compounds of formulae (V) and (VI) is subsequently functionally modified.

10. A composition suitable for medicinal use which comprises a pharmaceutically effective amount of at least one compound as defined in claim 1 in a pharmaceutically acceptable base.

11. A composition according to claim 10 suitable for topical use in which the concentration of said compound is 0.0005% to 2% by weight.

12. A composition according to claim 11 in which the concentration of said compound is 0.002% to 1% by weight.

13. A composition according to claim 11 which is in the form of an unguent, a gel, a cream, an ointment, a powder, a dyeing composition, a solution, a suspension, an emulsion, a lotion, a spray, an adhesive patch or an impregnated pad.

14. A composition according to claim 10 suitable for oral use.

15. A composition according to claim 14 which is in the form of gelatin capsules containing from 0.1 mg to 1 mg of said compound.

16. A composition according to claim 14 which is in the form of a solution or suspension intended to be administered parenterally.

17. A composition according to claim 16 which contains from 0.01 to 1 mg of said compound per ml of solution or suspension.

18. A composition according to claim 10 suitable for administering to the eye in the form of eye drops.

19. A composition according to claim 10 in which the pharmaceutically acceptable base comprises at least one of water, gelatin, lactose, starch, talc, liquid petrolatum, gum arabic, a polyalkylene glycol, magnesium stearate, a diluent, solvent or thickener.

20. A composition suitable for cosmetic use which comprises a cosmetically effective amount of at least one compound as defined in claim 1 in a cosmetically acceptable base.

21. A composition according to claim 20 in which the concentration of said compound is 0.0005 to 2% by weight.

22. A composition according to claim 21 in which the concentration of said compound is 0.01% to 1% by weight.

23. A composition according to claim 20 which is in the form of a lotion, gel, cream, soap or shampoo.

24. A composition according to claim 10 which contains at least one additive selected from the group consisting of moisturising agents, antiseborrhoeic agents, anti-acne agents, antibiotics, agents which encourage fresh growth of hair, anti-inflammatory agents, carotenoids, antipsoriatic agents, flavouring, preservatives, stabilisers, moisture regulators, pH regulators, osmotic pressure modifiers, emulsifiers, UV-A and UV-B filters and antioxidants 25. A method of treating a patient with a dermatological condition which comprises administering to the patient a composition as defined in claim 10.

26. A compound of the formula

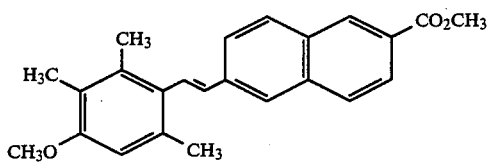

27. A compound of the formula

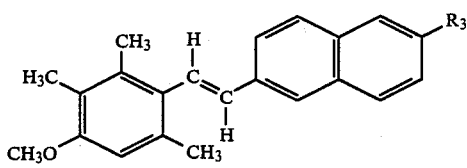

wherein
R$_3$ represents

wherein R$_5$ represents
(a) hydrogen, alkyl having 1-4 carbon atoms, —NR'R" wherein R' and R" each independently represent hydrogen, alkyl having 1-4 carbon atoms, alkenyl having 3-4 carbon atoms, cyclopentyl, cyclohexyl, aralkyl or aryl, or R' and R" together with the nitrogen atom to which they are attached form a heterocycle, or NR'R" represents amino acid or glucosamine residue, or
(b) —OR$_6$ wherein R$_6$ represent hydrogen, alkyl having 1-18 carbon atoms, monohydroxyalkyl wherein the alkyl moiety has 2-3 carbon atoms, polyhydroxyalkyl containing 2-5 hydroxyl groups and wherein the alkyl moiety has 3-6 carbon atoms.

28. A compound of the formula

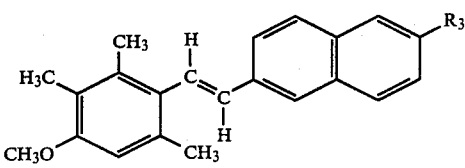

wherein
R$_3$ represents

wherein R$_5$ represents —OR$_6$ wherein R$_6$ represents hydrogen, alkyl having 1-18 carbon atoms, monohydroxyalkyl wherein the alkyl moiety has 2-3 carbon atoms, polyhydroxyalkyl containing 2-5 hydroxyl groups and wherein the alkyl moiety has 3-6 carbon atoms.

29. The compound of claim 28 wherein R$_6$ represents alkyl having 1-18 carbon atoms.

* * * * *